US012753146B2

(12) United States Patent
Lattuada et al.

(10) Patent No.: US 12,753,146 B2
(45) Date of Patent: Oct. 6, 2026

(54) INDUSTRIAL SYNTHESIS OF SERINOL

(71) Applicant: BRACCO IMAGING SPA, Milan (IT)

(72) Inventors: Luciano Lattuada, Cassina de'Pecchi (IT); Giovanni Battista Giovenzana, Novara (IT); Camilla Cavallotti, Novara (IT); Ivan Menegotto, Borgomanero (IT)

(73) Assignee: BRACCO IMAGING S.P.A., Milan (IT)

(*) Notice: Subject to any disclaimer, the term of this patent is extended or adjusted under 35 U.S.C. 154(b) by 443 days.

(21) Appl. No.: 18/283,125

(22) PCT Filed: Mar. 21, 2022

(86) PCT No.: PCT/EP2022/057290
§ 371 (c)(1),
(2) Date: Sep. 20, 2023

(87) PCT Pub. No.: WO2022/200247
PCT Pub. Date: Sep. 29, 2022

(65) Prior Publication Data

US 2024/0199530 A1 Jun. 20, 2024

(30) Foreign Application Priority Data

Mar. 22, 2021 (EP) .................................... 21163929

(51) Int. Cl.

| | |
|---|---|
| ***C07C 213/02*** | (2006.01) |
| ***C07C 231/02*** | (2006.01) |
| ***C07C 231/12*** | (2006.01) |
| ***C07D 263/24*** | (2006.01) |

(52) U.S. Cl.
CPC .......... *C07C 213/02* (2013.01); *C07C 231/02* (2013.01); *C07C 231/12* (2013.01); *C07D 263/24* (2013.01)

(58) Field of Classification Search
CPC .................................................... C07C 213/02
See application file for complete search history.

(56) References Cited

U.S. PATENT DOCUMENTS

| | | | |
|---|---|---|---|
| 4,001,323 | A | 1/1977 | Felder et al. |
| 4,221,740 | A | 9/1980 | Pfeiffer |
| 4,503,252 | A | 3/1985 | Felder et al. |
| 5,023,379 | A | 6/1991 | Felder et al. |

FOREIGN PATENT DOCUMENTS

| | | | |
|---|---|---|---|
| EP | 1156042 | A1 | 11/2001 |
| JP | 2007039347 | A * | 2/2007 |
| WO | 1995028379 | A1 | 10/1995 |
| WO | 2002044125 | A1 | 6/2002 |
| WO | 2012175903 | A1 | 12/2012 |
| WO | 2015067601 | A1 | 5/2015 |

OTHER PUBLICATIONS

Indran "An accelerated route of glycerol carbonate formation from glycerol using waste boiler ash as catalyst" RSC Advances (2014), 4(48), 25257-25267.*
Kim "Synthesis of glycerol carbonate from urea and glycerol using polymer-supported metal containing ionic liquid catalysts" Appl. Catal., A, 2014, 473,31-40.*
"Iopamidol," In: The Merck Index, RSC Publishing, 15th Ed., pp. 940-941 (2013).
Andressen, B. et al., "Serinol: small molecule—big impact," AMB Express, available at: http://www.amb-express.com/content/1/1/12 (2011).
Dibenedetto, A., et al., "Catalytic Synthesis of Hydroxymethyl-2-oxazolidinones from Glycerol or Glycerol Carbonate and Urea," ChemSusChem, 6:345-352 (2013).
Hammond, C., et al., "Synthesis of glycerol carbonate from glycerol and urea with gold-based catalysts," Dalton Trans., 40:3927-3937 (2011).
International Search Report and Written Opinion for PCT/EP2022/057290, mailed Aug. 8, 2022.
Jost, U., et al., "Downstream processing of serinol from a glycerol-based fermentation broth and transfer to other amine containing molecules," Eng. Life Sci., 17:479-488 (2017).
Luo, X., et al., "Value-added processing of crude glycerol into chemicals and polymers," Biores. Technol., 215:144-154 (2016).
Lusic, H. et al., "X-ray-Computed Tomography Contrast Agents," Chem. Rev., 113, 1641-1666 (2013).
Meessen, J.H., "Urea," In: Ulmann's Encyclopedia of Industrial Chemistry, Wiley VCH, pp. 657-695 (2012).
Nguyen-Phu, H., et al., "Disordered structure of ZnAl2O4 phase and the formation of a Zn NCO complex in ZnAl mixed oxide catalysts for glycerol carbonylation with urea," Journal of Catalysis, 373:147-160 (2019).

(Continued)

Primary Examiner — David K O'Dell
(74) *Attorney, Agent, or Firm* — VIVICAR Law, PLLC

(57) ABSTRACT

The present invention is related to the synthesis of 4-hydroxymethyl-2-oxazolidinone (serinol carbamate, SC), which can be subsequently hydrolyzed to 2-amino-1,3-propanediol (serinol), by reacting glycerol and urea: (I) In general, glycerol is heated with urea and a catalyst, with or without a solvent, to give mainly 4-hydroxymethyl-2-oxazolidinone (serinol carbamate, SC), which is hydrolyzed in the next step to 2-amino-1,3-propanediol (serinol). Alternatively, glycerol 1,2-carbonate can be used instead of glycerol. Serinol obtained by the process of the invention may be used in the synthesis of Iopamidol.

(I)

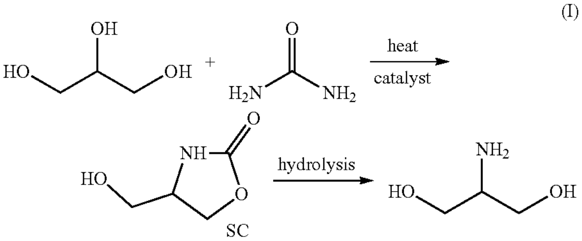

SC

20 Claims, No Drawings

(56) References Cited

OTHER PUBLICATIONS

Nguyen-Phu, H., et al., "Investigating time-dependent Zn species over Zn-based catalysts in glycerol carbonylation with urea and their roles in the reaction mechanism," Applied Catalysis A, 561:28-40 (2018).

Pallavicini, M., et al., "Resolution of 5-hydroxymethyl-2-oxazolidinone by preferential crystallization and investigations on the nature of the racemates of some 2-oxazolidinone derivatives," Tetrahedron Asymmetry, 15:1659-1665 (2004).

Razali, N.A., et al., "The role of impurities in the La2O3 catalysed carboxylation of crude glycerol," Catalysis Letters, 149:1403-1414 (2019).

Turney, T.W., et al., "Formation of glycerol carbonate from glycerol and urea catalysed by metal monoglycerolates," Green Chem., 15:1925-1931 (2013).

Zhang, J., et al., "Lanthanum-based mixed oxides for the synthesis of glycerol carbonate from glycerol and urea," Reac. Kinet. Mech. Cat., 113:375-392 (2014).

* cited by examiner

INDUSTRIAL SYNTHESIS OF SERINOL

CROSS-REFERENCE TO RELATED APPLICATIONS

This application is the national stage application of corresponding international application number PCT/EP2022/057290, filed Mar. 21, 2022, which claims priority to and the benefit of European application no. 21163929.9, filed Mar. 22, 2021, which is hereby incorporated by reference in its entirety.

The invention relates to a new synthetic process for the preparation of serinol carbamate and its conversion to serinol (2-amino-1,3-propanediol). In addition, the invention relates to the use of serinol produced by the process of the invention in the synthesis of Iopamidol, an iodinated X-ray contrast agent.

BACKGROUND OF THE INVENTION

Serinol (2-amino-1,3-propanediol) is a high-value building block which finds many applications in the pharmaceutical field, for example in the manufacturing of the non-ionic X-ray contrast agent Iopamidol, and more generally in the chemical industry.

Iopamidol is a radiographic contrast agent well known and widely used in daily diagnostic practice (The Merck Index, RSC Publishing, 15th Ed., 2013, 940-941; Lusic, H. et al., Chem. Rev. 2013, 113, 1641-1666).

The industrial synthesis of Iopamidol is shown in Scheme 1 and described, for example, in U.S. Pat. No. 4,001,323.

Scheme 1

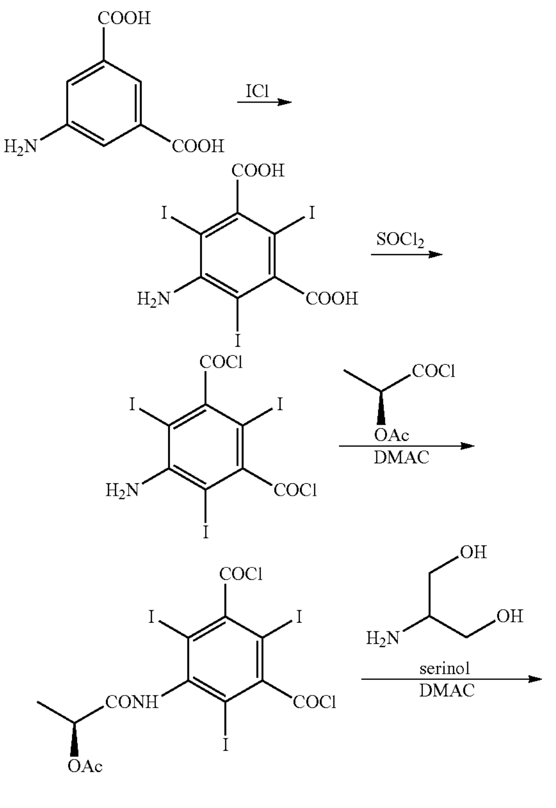

-continued

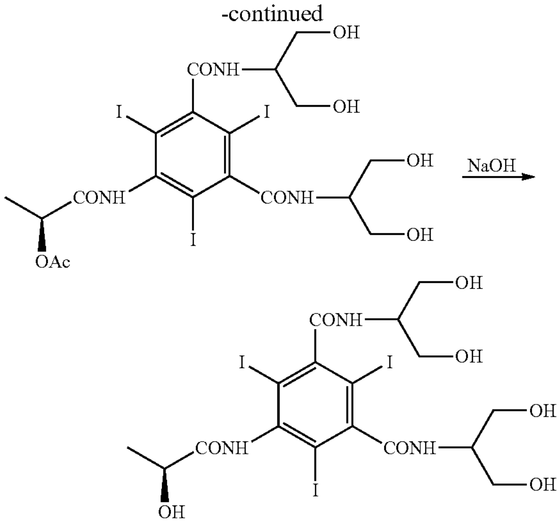

Iopamidol

Serinol is typically prepared by chemical synthesis through several alternative ways or, more recently, by biocatalysis exploiting the activity of specific enzymes. Most of these known processes have been reviewed (Andressen B. et al, AMB Express 2011, 1-12).

The approaches reported in literature display several drawbacks such as low yields, use of costly, toxic or dangerous reagents, issues in the work-up, formation of serinol/isoserinol mixtures difficult to separate and to purify.

For example, an industrial process (see U.S. Pat. No. 4,221,740) starts from nitromethane, which may be explosive, and formaldehyde, which is carcinogen, and the intermediate is hydrogenated in the presence of heavy metals as catalysts. The presence of traces of these metals in serinol may be a problem for their toxicity, especially if serinol is employed for pharmaceutical syntheses. In other processes, dihydroxyacetone is reacted with ammonia (see U.S. Pat. No. 5,023,379) or hydroxylamine (see WO9528379), both having toxic concerns, and again the intermediate is hydrogenated in the presence of heavy metals. In a different process epichlorohydrin, known to be carcinogen, was used as starting material (see U.S. Pat. No. 4,503,252). Furthermore, it is possible to prepare serinol with biotechnological approaches starting from renewable resources, but these processes are characterized by low productivity and difficult isolation of the product from the fermentation broth (Jost U. et al, Eng. Life Sci. 2017, 17, 479-488).

Therefore, it would be highly desirable to find a green, safe and efficient process working in mild conditions, with cheap and readily available reagents and applicable to a large industrial scale.

It has now been found that serinol can be efficiently synthesized by reaction of glycerol, or glycerol 1,2-carbonate, and urea in the presence of specific catalysts to form serinol carbamate (SC) which is then hydrolyzed to give serinol.

Glycerol and urea are two safe and low-cost commodities; the first one is for instance a by-product of biodiesel production process (Luo X. et al, Biores. Technol. 2016, 215, 144-154) while the second is produced on a large scale to be employed mainly as fertilizer (Meessen J. H., Urea, Ulmann's Encyclopedia of Industrial Chemistry, Wiley VCH, 2012, 657-695).

The reaction of glycerol with urea in the presence of a catalyst is widely known for the preparation of glycerol carbonate (see for instance EP1156042), whilst a yield of only 25% has been reported carrying out the same reaction in the absence of a catalyst (Turney T. W. et al, Green Chem. 2013, 15, 1925-1931).

Dibenedetto et al., ChemSusChem 2013, 6, 345-352 discloses the reaction of glycerol with urea to give serinol carbamate (SC) and isoserinol carbamate (ISC). The reaction was performed at 180° C. under vacuum for 4 h. Among the different metal oxides tested as catalysts, only γ-Zr phosphate showed a moderate activity; however, it provided with a poor yield of 14% a mixture of serinol carbamate (SC) and isoserinol carbamate (ISC) in a ratio of 1/7 (with the preferential formation of the regioisomer ISC).

Nguyen-Phu H. et al, Applied Catalysis A 2018, 561, 28-40 and Nguyen-Phu H. et al, Journal of Catalysis 2019, 373, 147-160 disclose Zn-based catalysts which showed a high selectivity to glycerol carbonate in the reaction of glycerol carbonylation with urea. In particular ZnAlO displayed a glycerol conversion of 91% after 4 hours at 140° C. Serinol carbamate however was obtained as by-product (IV), with a selectivity of 17% only.

Razali N. A. et al., Catalysis Letters 2019, 149, 1403-1414 discloses the use of $La_2O_3$ as heterogeneous catalyst for the carboxylation of glycerol to give glycerol carbonate and, as co-products, serinol and isoserinol carbamates (FIG. 4). The conversion yields of glycerol however are quite low and no data are provided with respect to the selectivity to serinol carbamate.

Hammond C. et al., Dalton Trans. 2011, 40, 3927-3937 discloses the use of an heterogeneous gold based catalyst supported on a range of oxides, such as for instance MgO, for the preparation of glycerol carbonate starting from glycerol and urea. In Table 1 it shows that, using MgO as catalyst support, 69% of glycerol is converted, however serinol carbamate (SC) is obtained only as by-product (7) with a selectivity of 10%.

Differently from the known processes, the process of the present invention is surprisingly able to provide selectively serinol carbamate (SC) as the main product over glycerol carbonate (GC) and over the regioisomer isoserinol carbamate (ISC). This is mainly achieved through the selection of the specific catalysts and reaction conditions of the invention, which have unexpectedly provided serinol carbamate with good yields and good selectivity results.

SUMMARY OF THE INVENTION

The present invention is related to the synthesis of 4-hydroxymethyl-2-oxazolidinone (serinol carbamate, SC), which can then be hydrolyzed to 2-amino-1,3-propanediol (serinol), by reacting glycerol and urea, as shown in Scheme 2.

Scheme 2

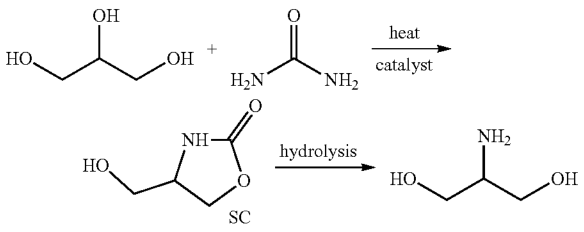

SC

In general, glycerol is heated with urea and a catalyst, with or without a solvent, to give 4-hydroxymethyl-2-oxazolidinone (serinol carbamate, SC) as main product, which is hydrolyzed in the next step to 2-amino-1,3-propanediol (serinol).

Alternatively, glycerol 1,2-carbonate (GC) can be used instead of glycerol as starting material.

DETAILED DESCRIPTION OF THE INVENTION

Object of the present invention is a process for preparing 4-hydroxymethyl-2-oxazolidinone (serinol carbamate) of formula (II):

(II)

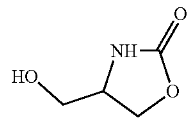

said process comprising the step of:

i) reacting glycerol or glycerol 1,2-carbonate with urea at a temperature higher than or equal to 130° C. in the presence of a catalyst selected from Mg, MgO, $Mg(OMe)_2$, $Mg(OH)_2$ and $La_2O_3$.

A further object of the present invention is the process as defined above further comprising the steps of:

ii) hydrolyzing 4-hydroxymethyl-2-oxazolidinone of formula (II) to obtain 2-amino-1,3-propanediol (serinol) of formula (I):

(I)

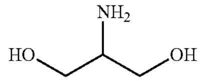

and iii) optionally converting 2-amino-1,3-propanediol of formula (I) in a salt thereof.

Step i)

The catalyst used in step i) is preferably selected from Mg, MgO, $Mg(OMe)_2$ and $Mg(OH)_2$. Most preferably it is Mg or MgO and even more preferably it is metallic Mg. Preferably metallic Mg is in powder form. The reaction of step i) may be carried out in solventless conditions (neat) or in the presence of an aprotic polar solvent having boiling point 130° C., preferably selected from the group consisting of diethylene glycol dimethyl ether (diglyme), diethylene glycol diethyl ether, diethylene glycol dibutyl ether, triethylene glycol dimethyl ether (triglyme), dipropylene glycol dimethyl ether (proglyde), isosorbide dimethyl ether, methoxybenzene (anisole), ethyl phenyl ether (phenetole), n-decane, n-dodecane, decahydronaphtalene (decalin), 1,2,3-trimethoxypropane and hexafluoropropene polyether.

Preferably, step i) is carried out in solventless conditions or in the presence of diethylene glycol dimethyl ether.

In one embodiment, step i) is carried out in solventless conditions with $Mg(OH)_2$ or Mg as catalyst.

In another embodiment, step i) is carried out in diethylene glycol dimethyl ether(diglyme) with Mg as catalyst.

The reaction of step i) is carried out at a temperature ranging from 130° C. to 200° C., preferably from 150° C. to 180° C. In particular, when no solvent is used, the reaction is preferably carried out at 180° C.

The reaction time may range from 1 hour to 20 hours, preferably from 4 hours to 8 hours.

Urea is preferably used in excess amount. The molar ratio urea/glycerol or urea/glycerol 1,2-carbonate preferably ranges from 1:1 to 4:1, more preferably it is 3:1.

The molar ratio catalyst/glycerol or catalyst/glycerol 1,2-carbonate preferably ranges from 0.1:1 to 1:1.

Step ii)

The hydrolysis of step ii) is preferably carried out in the presence of an aqueous solution comprising a base selected from metal hydroxides such as LiOH, NaOH, KOH, $Ca(OH)_2$ and $Ba(OH)_2$, preferably NaOH or KOH.

Preferably the hydrolysis is carried out in water or in a mixture of an alcohol and water such as MeOH/water, EtOH/water or 2-propanol/water.

The hydrolysis step is preferably performed at reflux.

In one embodiment, the product obtained in step i) is directly used in step ii) after water addition and filtration to eliminate the insoluble catalyst and without any further purification step.

Step iii)

When 2-amino-1,3-propanediol is converted in form of a salt, the salt is preferably chloride or oxalate. The salt of 2-amino-1,3-propanediol may be obtained for instance by treatment with hydrochloric acid or oxalic acid dihydrate.

A further object of the present invention is the use of serinol produced by the process of the invention in the synthesis of Iopamidol.

In one embodiment it is provided a process for obtaining Iopamidol of formula (III):

(III)

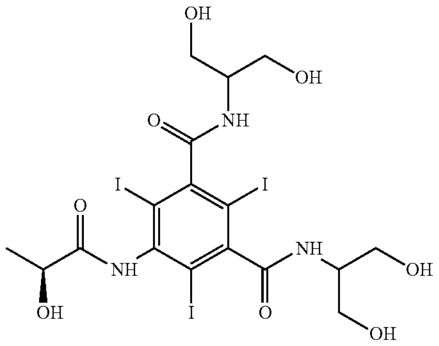

said process comprising the step of preparing the intermediate of formula (IV):

(IV)

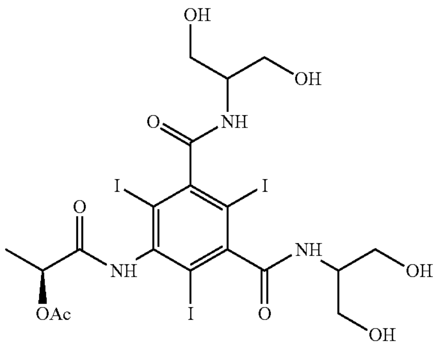

by reacting 2-amino-1,3-propanediol obtained by the process described above with the compound of formula (V):

(V)

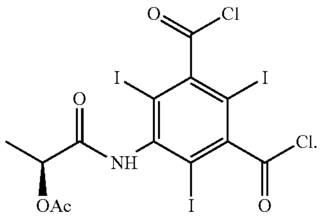

The procedures and reaction conditions are disclosed, for example, in U.S. Pat. No. 4,001,323.

Accordingly, an object of the invention is a process for the preparation of Iopamidol (III) comprising the following steps:

i) reacting glycerol or glycerol 1,2-carbonate with urea at a temperature higher than or equal to 130° C. in the presence of a catalyst selected from Mg, MgO, $Mg(OMe)_2$, $Mg(OH)_2$ and $La_2O_3$ thus obtaining the compound of formula (II)

(II)

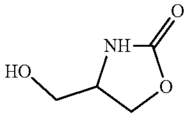

ii) hydrolyzing the compound of formula (II) to obtain 2-amino-1,3-propanediol (serinol) of formula (I):

(I)

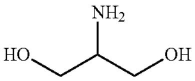

iv) reacting the compound of formula (I) thus obtained with the compound of formula (V)

v) hydrolyzing the resultant compound of formula (IV)

(IV)

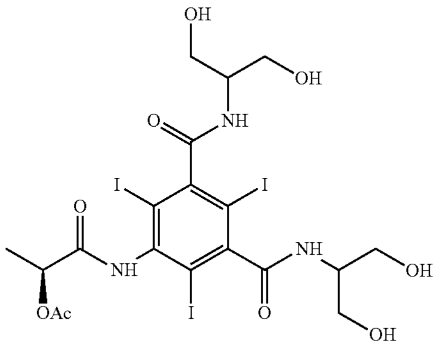

by removing the acetyl protecting group.

v) hydrolyzing the resultant compound of formula (IV)

(IV)

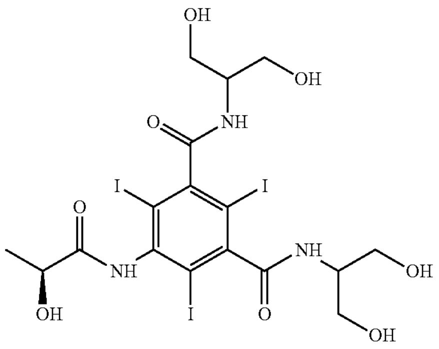

by removing the acetyl protecting group.

Preferably, step i) is carried out in solventless conditions (neat) or in the presence of an aprotic polar solvent having boiling point 130° C., preferably selected from the group consisting of diethylene glycol dimethyl ether (diglyme), diethylene glycol diethyl ether, diethylene glycol dibutyl ether, triethylene glycol dimethyl ether (triglyme), dipropylene glycol dimethyl ether (proglyde), isosorbide dimethyl ether, methoxybenzene (anisole), ethyl phenyl ether (phenetole), n-decane, n-dodecane, decahydronaphtalene (decalin), 1,2,3-trimethoxypropane and hexafluoropropene polyether.

More preferably step i) is carried out using Mg as catalyst and diethylene glycol dimethyl ether (diglyme) as solvent or in solventless conditions.

Preferably, the molar ratio urea/glycerol or urea/glycerol 1,2-carbonate in step i) ranges from 1:1 to 4:1, more preferably it is 3:1. In one embodiment the ratio catalyst/glycerol or catalyst/glycerol 1,2-carbonate in step i) ranges from 0.1:1 to 1:1.

In another embodiment step i) is carried out at a temperature ranging from 130° C. to 200° C., preferably from 150° C. to 180° C.

A further object of the present invention is a process for obtaining Iopamidol of formula (III) comprising the step of preparing the intermediate of formula (VI):

(VI)

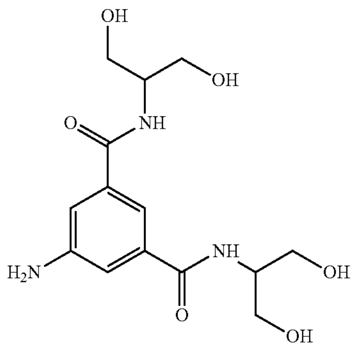

by reacting 2-amino-1,3-propanediol obtained by the process described above with a compound of formula (VII):

(VII)

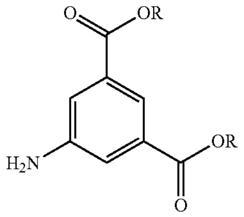

wherein R is a straight or branched $C_1$-$C_4$ alkyl group. The steps and conditions for the reaction with the above compound (VII) are described, for example, in WO0244125 or WO2015067601.

Accordingly, it is an object of the present invention a process the preparation of Iopamidol (III) comprising the following steps:

i) reacting glycerol or glycerol 1,2-carbonate with urea at a temperature higher than or equal to 130° C. in the presence of a catalyst selected from Mg, MgO, $Mg(OMe)_2$, $Mg(OH)_2$ and $La_2O_3$ thus obtaining the compound of formula (II)

(II)

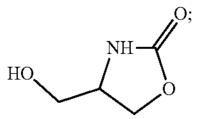

ii) hydrolyzing the compound of formula (II) to obtain 2-amino-1,3-propanediol (serinol) of formula (I):

(I)

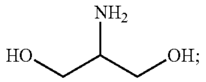

vi) reacting the compound of formula (I) thus obtained with the compound of formula (VII)

(VII)

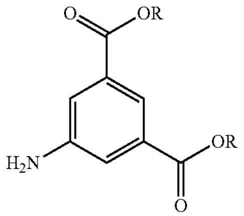

wherein R is a straight or branched $C_1$-$C_4$ alkyl group, to provide the 5-amino-N,N'-bis[2-hydroxy-1-(hydroxymethyl)ethyl]-1,3-benzenedicarboxamide (VI)

(VI)

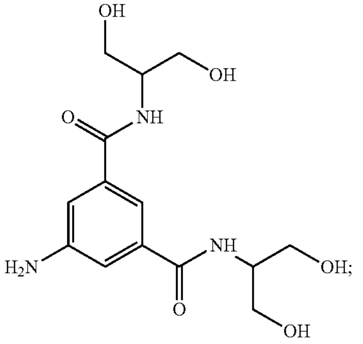

vii) iodinating the compound (VI) at positions 2, 4, 6 to provide the 5-amino-N,N'-bis[2-hydroxy-1-(hydroxymethyl)ethyl]-2,4,6-triiodo-1,3-benzenedicarboxamide (VIII)

(VIII)

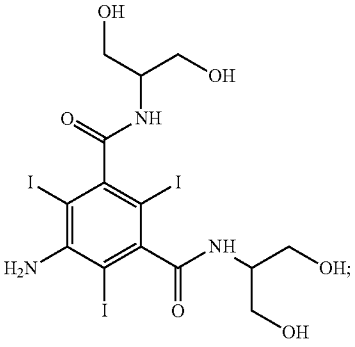

viii) treating compound (VIII) with a boronic acid, a borate ester or a boroxine to provide the corresponding compound (IX)

(IX)

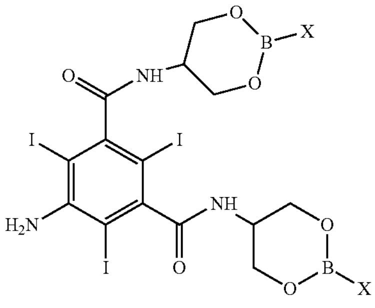

wherein X is —$OR_2$ or —$R_3$ and wherein $R_2$ and $R_3$ are a $C_1$-$C_6$ linear or branched alkyl, $C_3$-$C_6$ cycloalkyl, $C_6$ aryl, optionally substituted with a group selected from methyl, ethyl, n-propyl, i-propyl, n-butyl, sec-butyl, t-butyl and phenyl;

ix) reacting the compound (IX) with the acylating agent (S)-2-(acetyloxy)propanoyl chloride and hydrolyzing the resultant intermediate to obtain Iopamidol (III). The above steps from vi) to ix) are preferably carried out according to the process described in WO2015/067601.

Preferred borates are selected from the group consisting of t-butyl-, n-propyl and ethyl borate. Esters with different alkyl groups can also be used.

Preferably, step i) is carried out in solventless conditions (neat) or in the presence of an aprotic polar solvent having boiling point 130° C., preferably selected from the group consisting of diethylene glycol dimethyl ether (diglyme), diethylene glycol diethyl ether, diethylene glycol dibutyl ether, triethylene glycol dimethyl ether (triglyme), dipropylene glycol dimethyl ether (proglyde), isosorbide dimethyl ether, methoxybenzene (anisole), ethyl phenyl ether (phenetole), n-decane, n-dodecane, decahydronaphtalene (decalin), 1,2,3-trimethoxypropane and hexafluoropropene polyether.

More preferably step i) is carried out using Mg as catalyst and diethylene glycol dimethyl ether (diglyme) as solvent or in solventless conditions.

Preferably, the molar ratio urea/glycerol or urea/glycerol 1,2-carbonate in step i) ranges from 1:1 to 4:1, more preferably it is 3:1.

In one embodiment the ratio catalyst/glycerol or catalyst/glycerol 1,2-carbonate in step i) ranges from 0.1:1 to 1:1.

In another embodiment step i) is carried out at a temperature ranging from 130° C. to 200° C., preferably from 150° C. to 180° C.

According to the present invention and differently from the processes of the prior art, 4-hydroxymethyl-2-oxazolidinone (II) (serinol carbamate) is obtained by a one-pot reaction and the obtained carbamate, after filtration of the catalyst, can be directly hydrolyzed to give 2-amino-1,3-propanediol.

As better illustrated in the following examples, the process of the present invention allows to obtain the 4-hydroxymethyl-2-oxazolidinone (II) (serinol carbamate) with a good yield while providing remarkable selectivity with respect to the regioisomer 5-hydroxymethyl-2-oxazolidinone (X) (isoserinol carbamate) and to glycerol 1,2-carbonate (XI)

(X)

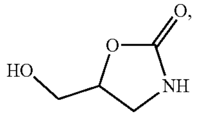

(XI)

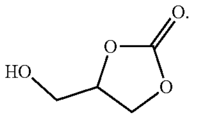

Moreover, after hydrolysis, good yields of 2-amino-1,3-propanediol (I) (serinol) are obtained; thus, it is provided a safe and efficient process working in mild conditions, with cheap and readily available reagents and applicable to a large industrial scale.

EXPERIMENTAL PART

List of Abbreviations

GC: glycerol 1,2-carbonate

ISC: isoserinol carbamate or 5-hydroxymethyl-2-oxazolidinone

SC: serinol carbamate or 4-hydroxymethyl-2-oxazolidinone

Analytical Method

The reaction products were analysed by Gas Chromatography using the following instrumental parameters:

| | |
|---|---|
| Capillary Column | J&W Scientific DB-23, 30 m, 0.25 mm, 0.25 μm |
| Carrier gas | He |
| Initial flow | 2.0 mL/min |
| Oven | T = heat from 50° C. to 250° C. (rate 15° C./min) and keep for 20 min |
| Detector | Flame Ionization Detector (FID) at 380° C. |
| Hydrogen flow | 30 mL/min |
| Air flow | 334 mL/min |
| Injection volume | 1.0 μL |

The data obtained by Gas Chromatography analysis are reported in area %.

An amount of serinol carbamate (SC) and isoserinol carbamate (ISC) was synthesized following the procedures reported in Pallavicini M. et al., Tetrahedron Asymmetry, 2004, 15, 1659-1665 and used as reference standard.

An amount of glycerol 1,2-carbonate (GC) was purchased from TCI Europe and used as reference standard.

Reagents, catalysts and solvents are commercially available: for instance, glycerol, diethylene glycol dimethyl ether (diglyme), triethylene glycol dimethyl ether (triglyme), $Mg(OH)_2$, and $La_2O_3$ were purchased from Aldrich, urea was purchased from Fluka, magnesium was purchased from Riedel de Haen, hexafluoropropene polyether (CAS Nr. 69991-67-9) was purchased from Fluorochem.

Solid $Mg(OMe)_2$ was obtained by evaporation of the methanolic solution (6-10%) purchased from Aldrich.

Example 1

Synthesis of Serinol Carbamate from Glycerol and Urea in Solventless Conditions (Neat)

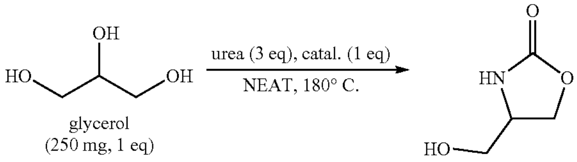 [SMILES: OCC(O)CO ; O=C1NC(CO)CO1]

glycerol
(250 mg, 1 eq)

A mixture of glycerol (250 mg, 2.72 mmol, 1 eq), urea (489 mg, 8.15 mmol, 3 eq) and magnesium methoxide (235 mg, 2.72 mmol, 1 eq) was heated at 180° C. for 7 hours, without any solvent. The mixture reaction was monitored by gas chromatography. The same reaction was performed with Mg as catalyst (7 mg, 0.27 mmol, 0.1 eq) for 4 hours, and the results are reported in Table 1, showing a yield of serinol carbamate (SC) higher than 75% (GC-FID peak area %) and a selectivity of serinol carbamate vs isoserinol carbamate of at least 5:1.

TABLE 1

| T (h) | Solvent | Catalyst | Glycerol | GC | SC | ISC |
|---|---|---|---|---|---|---|
| 7 h | Neat | $Mg(OMe)_2$ (1 eq) | 6.1% | 3.4% | 75.8% | 14.7% |
| 4 h | Neat | Mg (0.1 eq) | 0.0% | 1.9% | 78.9% | 12.0% |

Example 2

Synthesis of Serinol Carbamate from Glycerol and Urea Using Different Catalysts in Diglyme

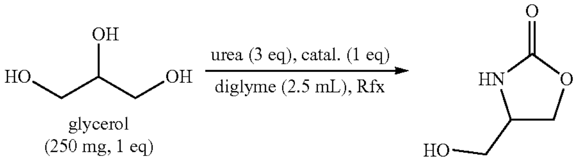 [SMILES: OCC(O)CO ; O=C1NC(CO)CO1]

glycerol
(250 mg, 1 eq)

A mixture of glycerol (250 mg, 2.72 mmol, 1 eq), diglyme (2.5 mL), urea (489 mg, 8.15 mmol, 3 eq) and a catalyst selected from Mg, MgO, $Mg(OH)_2$, $Mg(OMe)_2$ and $La_2O_3$ (1 eq) was heated at reflux for 4 hours. The mixture was monitored by gas chromatography. The results obtained using the above different catalysts in diglyme, are reported in Table 2, showing a yield of serinol carbamate (SC) higher than 44% (GC-FID peak area %) and a selectivity of serinol carbamate vs isoserinol carbamate ranging up to about 12:1.

TABLE 2

| T (h) | Solvent | Catalyst | Glycerol | GC | SC | ISC |
|---|---|---|---|---|---|---|
| 18 h | Diglyme | $Mg(OMe)_2$ | 0.0% | 28.7% | 64.0% | 7.3% |
| 4 h | Diglyme | $Mg(OH)_2$ | 1.8% | 4.0% | 49.4% | 42.4% |
| 4 h | Diglyme | Mg | 0.2% | 0.5% | 82.8% | 7.2% |
| 4 h | Diglyme | MgO | 0.0% | 0.0% | 82.4% | 17.6% |
| 4 h | Diglyme | $La_2O_3$ | 1.3% | 22.4 | 43.8% | 31.9% |

Example 3

Synthesis of Serinol Carbamate from Glycerol and Urea in Diglyme Using a Catalytic Amount of Mg

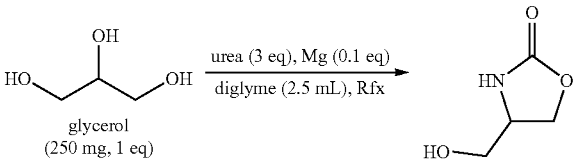 [SMILES: OCC(O)CO ; O=C1NC(CO)CO1]

glycerol
(250 mg, 1 eq)

A mixture of glycerol (250 mg, 2.72 mmol, 1 eq), diglyme (2.5 mL), urea (489 mg, 8.15 mmol, 3 eq) and magnesium powder (7 mg, 0.27 mmol, 0.1 eq) was heated at reflux. The mixture was monitored by gas chromatography. The results obtained after 4 h of reaction are reported in Table 3, showing a complete conversion of glycerol, with yield of serinol carbamate (SC) higher than 70% (GC-FID peak area %) and a selectivity of serinol carbamate vs isoserinol carbamate of about 6:1.

TABLE 3

| T (h) | Catalyst | Glycerol | GC | SC | ISC |
|---|---|---|---|---|---|
| 4 | Mg 0.1 eq | 0.0% | 16.7% | 70.5% | 11.4% |

Example 4

Synthesis of Serinol Carbamate from Glycerol and Urea in Proglyde Using Mg as Catalyst

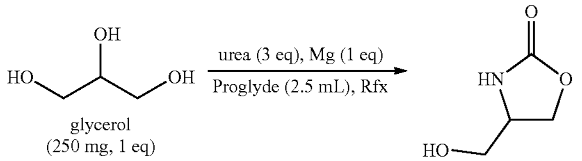 [SMILES: OCC(O)CO ; O=C1NC(CO)CO1]

Glycerol (250 mg, 2.72 mmol, 1 eq) was suspended in dipropylene glycol dimethyl ether (Proglyde™, 2.5 mL), urea (489 mg, 8.15 mmol, 3 eq) and magnesium powder (66 mg, 2.72 mmol, 1 eq) were added and the mixture reaction was heated at reflux. The reaction was monitored by gas chromatography. The results obtained after 4 h of reaction are reported in Table 4, showing a yield of serinol carbamate (SC) of about 86% (GC-FID peak area %) and a selectivity of serinol carbamate vs isoserinol carbamate of about 12:1.

TABLE 4

| T. (h) | Catalyst | Glycerol | GC | SC | ISC |
|---|---|---|---|---|---|
| 4 | Mg (1eq) | 3.9% | 2.9% | 85.8% | 7.4% |

Example 5

Synthesis of Serinol Carbamate from Glycerol 1,2-Carbonate in Diglyme

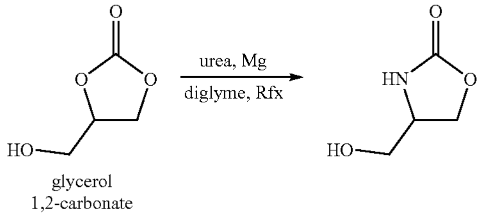 [SMILES: O=C1OCC(CO)O1 ; O=C1NC(CO)CO1]

A mixture of glycerol 1,2-carbonate (2.50 g, 21.2 mmol, 1.0 eq.), diglyme (10 mL), urea (3.80 g, 63.6 mmol, 3.0 eq) and magnesium powder (0.50 g, 21.2 mmol, 1.0 eq) was heated to reflux and stirred, monitoring the conversion by gas chromatography. The results obtained after 4 h of reaction are reported in Table 5, showing a complete conversion of glycerol 1,2-carbonate with a yield of serinol carbamate (SC) higher than 97% (GC-FID peak area %) and a selectivity of serinol carbamate vs isoserinol carbamate of about 65:1.

TABLE 5

| T. (h) | Catalyst | Glycerol | GC | SC | ISC |
|---|---|---|---|---|---|
| 4 | Mg (1eq) | 0.0% | 0.1% | 97.4% | 1.5% |

Example 6

Synthesis of Serinol Carbamate from Glycerol and Urea Using Mg as Catalyst in Different Solvents A mixture of glycerol (250 mg, 2.72 mmol, 1 eq), Mg (1 eq), urea (489 mg, 8.15 mmol, 3 eq) and a solvent selected from diethylene glycol dimethyl ether (diglyme), diethylene glycol diethyl ether, diethylene glycol dibutyl ether, triethylene glycol dimethyl ether (triglyme), isosorbide dimethyl ether, dipropylene glycol dimethyl ether (proglyde), methoxybenzene (anisole) and ethyl phenyl ether (phenetole) (2.5 mL) was heated at a temperature selected in a range from 130° C. and 200° C. (depending on the solvent) and stirred. The mixture was monitored by gas chromatography. The results obtained after 4 hours of reaction with the different solvents are reported in Table 6. The yields of serinol carbamate (SC) were higher than 55% (GC-FID peak area %), with selectivity of serinol carbamate vs isoserinol carbamate up to about 50:1.

TABLE 6

| Solvent | Glycerol | GC | SC | ISC |
|---|---|---|---|---|
| Diethylene glycol diethyl ether (diglyme) | 0.2% | 0.5% | 82.8% | 7.2% |
| Diethylene glycol diethyl ether | 8.2% | 0.0% | 54.7% | 1.1% |
| Diethylene glycol dibutyl ether | 19.3% | 1.4% | 57.9% | 5.9% |
| Triethylene glycol dimethyl ether (triglyme) | 2.2% | 1.0% | 79.9% | 13.4% |
| Isosorbide dimethyl ether | 3.1% | 22.5% | 54.5% | 19.8% |
| Dipropylene glycol dimethyl ether (proglyde) | 3.9% | 2.9% | 85.8% | 7.4% |
| Methoxybenzene (anisole) | 0.3% | 1.3% | 84.5% | 5.7% |
| Ethyl phenyl ether (phenetole) | 0.0% | 0.0% | 64.1% | 12.7% |

Example 7

Synthesis of Serinol from Glycerol and Urea in Diglyme

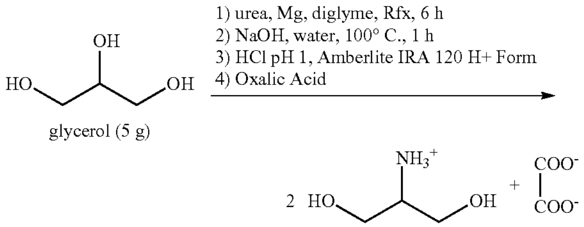

A mixture of glycerol (5.0 g, 54.3 mmol, 1 eq.), diglyme (10 mL), urea (9.8 g, 163 mmol, 3 eq) and magnesium powder (1.3 g, 54.3 mmol, 1 eq) was heated to reflux and stirred, monitoring the conversion by gas chromatography. After 6 hours, the reaction mixture was cooled and water (20 mL) was added, stirring for additional 15 minutes. The mixture was filtered to remove magnesium and a small amount of insoluble residue. Sodium hydroxide (10.9 g, 272 mmol, 5 eq) was added to the filtrate and the mixture was heated to 100° C. for 1 hour. Water and the organic solvent were evaporated in vacuum and the solid residue was suspended in methanol (20 mL) and stirred at room temperature for 8 hours. The insoluble residue was filtered on a Buchner funnel and the filtrate evaporated in vacuum. The residue has been redissolved in water (50 mL), acidified to pH 1 with conc. HCl and concentrated to half-volume by evaporation in vacuum. The solution was charged on a column filled with Amberlite IRA 120 ($H^+$-form, 450 mL bed volume). The column was eluted with water to remove inorganic salts, then with 1 M ammonium hydroxide to elute the product. The fractions of eluate containing the product were pooled and evaporated in vacuum. The residue was taken up in water (10 mL), heated to 80° C. and oxalic acid dihydrate was added. The solution was left overnight at room temperature and the white crystalline precipitate was collected. The crude serinol oxalate was recrystallised by water/ethanol at −5° C., leading to analytically pure serinol oxalate (1.1 g).

Example 8

Synthesis of Serinol from Glycerol and Urea in Diglyme

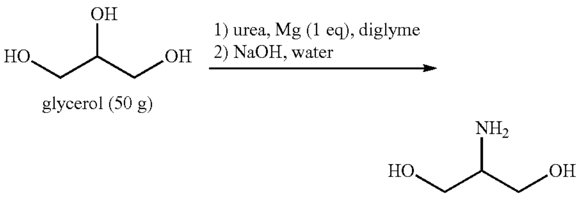

Urea (97.9 g, 1.63 mol, 3 eq) and magnesium powder (10 g, 0.413 mol, 0.8 eq) were added to a mixture of glycerol (50 g, 0.543 mol, 1 eq.) and diglyme (100 mL). The mixture was heated to reflux and stirred, monitoring the conversion by gas chromatography.

When the reaction was completed, water (200 mL) was added stirring for additional 15 minutes. The mixture was filtered to remove magnesium and the insoluble residue. NaOH (65.18 g, 1.63 mol, 3 eq) was added to the filtrate and the mixture was heated to 100° C. for 4 h. Water and diglyme were evaporated under reduced pressure, the solid residue was suspended in methanol and stirred at room temperature for a night. The insoluble residue was filtered on a Buchner funnel and the filtrate evaporated in vacuum. Active carbon (10% w/w) was added to the residue dissolved in water (250 mL) and acidified to pH 1 with conc. HCl. The suspension was heated at 80° C. for 1 h under magnetic stirring, then filtered on celite and washed with water. The filtrate was concentrated to half volume and charged on a column filled with an ion exchange resin, Amberlite IRA 120 ($H^+$-form, 2 L bed volume). The column was eluted with water to neutral pH and then with 1 M aqueous ammonia. The eluted fractions containing the product were pooled and evaporated in vacuum. The product was obtained as a yellow oil (40.74 g, 82.3% total yield, 5.5/1 serinol/isoserinol ratio).

Example 9

Synthesis of Serinol from Glycerol and Urea in Diglyme

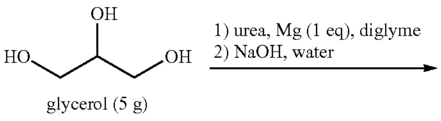

-continued

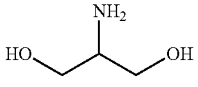

Urea (9.79 g, 163 mmol, 3 eq) and magnesium powder (1.0 g, 41.3 mmol, 0.8 eq) were added to a mixture of glycerol (5 g, 54.3 mmol, 1 eq.) and diglyme (10 mL). The mixture was heated to reflux for 4 h and stirred, monitoring the conversion by gas chromatography.

When the reaction was completed, water (20 mL) was added stirring for additional 15 minutes. The mixture was filtered to remove magnesium and the insoluble residue. NaOH (6.5 g, 163 mmol, 3 eq) was added to the filtrate and the mixture was heated to 100° C. for 1 h. Water and diglyme were evaporated under reduced pressure, the solid residue was suspended in methanol (50 ml) and stirred at room temperature for a night. The solid residue was filtered on a Buchner funnel and the filtrate evaporated in vacuum. The residue was dissolved in water (50 mL), acidified to pH 4.5 with conc. HCl, concentrated to half volume and charged on a column filled with an ion exchange resin, Amberlite IRA 120 ($H^+$-form, 200 mL bed volume). The column was eluted with water to neutral pH and then with 1 M aqueous ammonia. The eluted fractions containing the product were pooled and evaporated in vacuum. The product was obtained as a yellow oil (3.3 g, 66% total yield, 94.5% purity by gas chromatography).

Example 10

Synthesis of Serinol from Glycerol and Urea in Diglyme

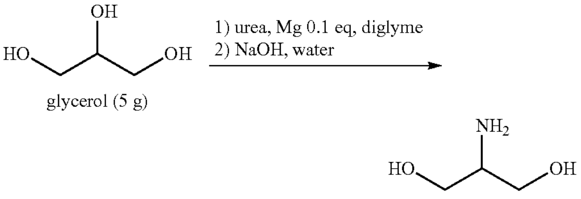

A mixture of glycerol (5.0 g, 54.3 mmol, 1 eq.), diglyme (10 mL), urea (9.8 g, 163 mmol, 3 eq) and magnesium powder (0.13 g, 5.4 mmol, 0.1 eq) was heated to reflux and stirred, monitoring the conversion by gas chromatography. The results obtained after 4 h are reported in Table 7.

TABLE 7

| T. (h) | Catalyst | Glycerol | GC | ISC | SC |
|---|---|---|---|---|---|
| 4 | Mg (0.1 eq) | 0.0% | 0.0% | 3.3% | 93.7% |

After 4 h, the reaction mixture was cooled and water (20 mL) was added, stirring for additional 15 minutes. The mixture was filtered to remove the unreacted magnesium and a small amount of insoluble residue. Sodium hydroxide (4.35 g, 109 mmol, 2 eq) was added to the filtrate and the mixture was heated to 100° C. for 1 h. Water and the organic solvent were evaporated in vacuum and the solid residue was suspended in methanol (20 mL) and stirred at room temperature for 8 h. The insoluble residue was filtered on a Buchner funnel and the filtrate was evaporated in vacuum.

The residue was redissolved in water (50 mL), acidified to pH 4.5 with conc. HCl and concentrated to half-volume by vacuum evaporation. The concentrated solution was charged on a column filled with Amberlite IRA 120 ($H^+$-form, 200 mL bed volume). The column was eluted with water to remove inorganic salts, then with 1 M ammonium hydroxide to elute the product. The fractions of elution containing the product were pooled and evaporated in vacuum obtaining a light-yellow viscous oil (3.1 g, 63% total yield, 96% purity by gas chromatography).

REFERENCES

1) The Merck Index, RSC Publishing, 15th Ed., 2013, 940-941
2) Lusic, H. et al., Chem. Rev. 2013, 113, 1641-1666
3) U.S. Pat. No. 4,001,323
4) Andressen B. et al, AMB Express 2011, 1-12
5) U.S. Pat. No. 4,221,740
6) U.S. Pat. No. 5,023,379
7) WO95/28379
8) U.S. Pat. No. 4,503,252
9) Jost U. et al, Eng. Life Sci. 2017, 17, 479-488
10) Luo X. et al, Biores. Technol. 2016, 215, 144-154
11) Meessen J. H., Urea, Ulmann's Encyclopedia of Industrial Chemistry, Wiley VCH, 2012, 657-695
12) EP 1156042
13) Turney T. W. et al, Green Chem. 2013, 15, 1925-1931
14) Dibenedetto et al., ChemSusChem 2013, 6, 345-352
15) Nguyen-Phu H. et al, Applied Catalysis A 2018, 561, 28-40
16) Nguyen-Phu H. et al, Journal of Catalysis 2019, 373, 147-160
17) Razali N. A. et al., Catalysis Letters 2019, 149, 1403-1414
18) Hammond C. et al., Dalton Trans. 2011, 40, 3927-3937
19) WO0244125
20) WO2015067601
21) Pallavicini M. et al., Tetrahedron Asymmetry, 2004, 15, 1659-1665

The invention claimed is:

1. A process for preparing 2-amino-1,3-propanediol (serinol) of formula (I):

(I)

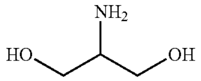

said process comprising the steps of:

i) reacting glycerol or glycerol 1,2-carbonate with urea at a temperature higher than or equal to 130° C. in the presence of a catalyst selected from Mg, MgO, $Mg(OMe)_2$, $Mg(OH)_2$ and $La_2O_3$, wherein the molar ratio urea/glycerol or urea/glycerol 1,2-carbonate ranges from 1:1 to 4:1, and wherein the ratio catalyst/glycerol or catalyst/glycerol 1,2-carbonate ranges from 0.1:1 to 1:1, to provide selectively 4-hydroxymethyl-2-oxazolidinone (serinol carbamate) of formula (II):

(II)

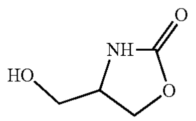

as the main product over glycerol carbonate and over isoserinol carbamate;

ii) hydrolyzing the serinol carbamate to obtain serinol; and iii) optionally converting the serinol into a salt thereof.

2. The process according to claim 1 wherein the catalyst used in step i) is selected from Mg, MgO, $Mg(OMe)_2$ and $Mg(OH)_2$.

3. The process according to claim 2 wherein the catalyst used in step i) is metallic Mg.

4. The process according to claim 1 wherein the reaction of step i) is carried out in solventless conditions.

5. The process according to claim 1 wherein the reaction of step i) is carried out in the presence of an aprotic polar solvent having a boiling point ≥130° C.

6. The process according to claim 5 wherein the solvent is selected from the group consisting of diethylene glycol dimethyl ether (diglyme), diethylene glycol diethyl ether, diethylene glycol dibutyl ether, triethylene glycol dimethyl ether (triglyme) dipropylene glycol dimethyl ether, isosorbide dimethyl ether, methoxybenzene (anisole), ethyl phenyl ether (phenetole), n-decane, n-dodecane, decahydronaphtalene, 1,2,3-trimethoxypropane and hexafluoropropene polyether.

7. The process according to claim 6 wherein the solvent is diethylene glycol dimethyl ether.

8. The process according to claim 1 wherein the reaction of step i) is carried out at a temperature ranging from 130° C. to 200° C.

9. The process according to claim 1 wherein the reaction of step i) is carried out at a temperature ranging from 150° C. to 180° C.

10. The process according to claim 1 wherein the molar ratio urea/glycerol or urea/glycerol 1,2-carbonate is 3:1.

11. The process according to claim 1 wherein the hydrolysis of step ii) is carried out in the presence of an aqueous solution comprising a base selected from alkali or alkaline earth metal hydroxides.

12. The process according to claim 11 wherein the base is LiOH, NaOH, KOH, $Ca(OH)_2$ or $Ba(OH)_2$.

13. A process for preparing Iopamidol of formula (III):

(III)

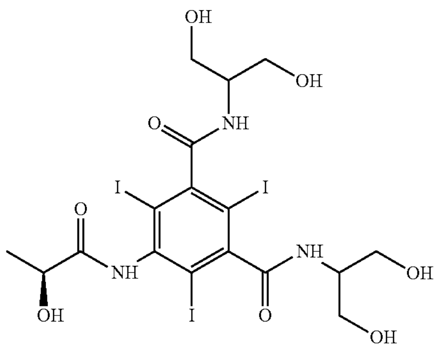

comprising the process according to claim 1 and further comprising the following steps:

iv) reacting the compound of formula (I) thus obtained with the compound of formula (V)

(V)

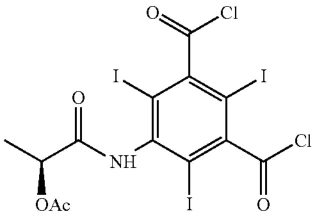

and v) hydrolyzing the resultant compound of formula (IV)

(IV)

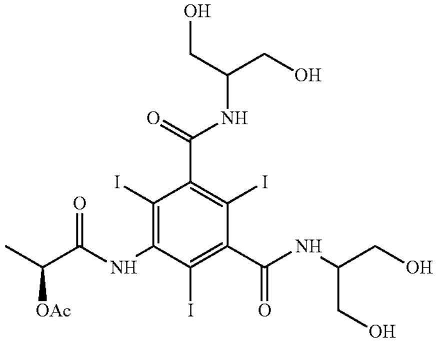

by removing the acetyl protecting group.

14. A process for preparing Iopamidol of formula (III):

(III)

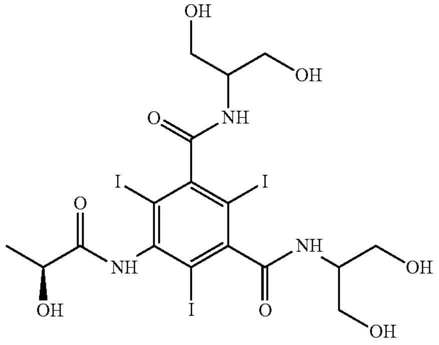

comprising the process according to claim 1 and further comprising the following steps:

vi) reacting the compound of formula (I) thus obtained with the compound of formula (VII)

(VII)

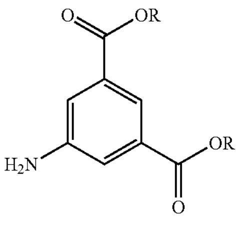

wherein R is a straight or branched $C_1$-$C_4$ alkyl group, to provide the 5-amino-N,N'-bis[2-hydroxy-1-(hydroxymethyl)ethyl]-1,3-benzenedicarboxamide (VI)

(VI)

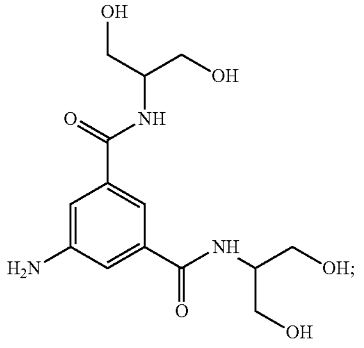

vii) iodinating the compound (VI) at positions 2,4,6 to provide the 5-amino-N,N'-bis[2-hydroxy-1-(hydroxymethyl)ethyl]-2,4,6-triiodo-1,3-benzenedicarboxamide (VIII)

(VIII)

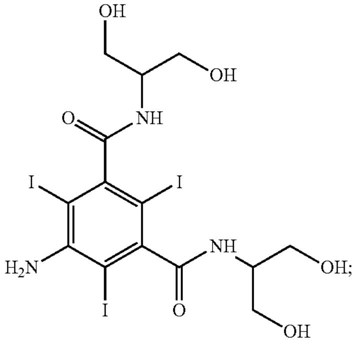

viii) treating compound (VIII) with a boronic acid, a borate ester or a boroxine to provide the corresponding compound (IX)

(IX)

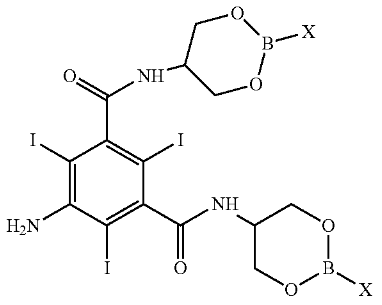

wherein X is —$OR_2$ or —$R_3$ and wherein $R_2$ and $R_3$ are a $C_1$-$C_6$ linear or branched alkyl, $C_3$-$C_6$ cycloalkyl, $C_6$ aryl, optionally substituted with a group selected from methyl, ethyl, n-propyl, i-propyl, n-butyl, sec-butyl, t-butyl and phenyl; and ix) reacting the compound (IX) with the acylating agent (S)-2-(acetyloxy) propanoyl chloride and hydrolyzing the resultant intermediate to obtain Iopamidol (III).

15. The process according to claim 11 wherein the base is NaOH or KOH.

16. A process for preparing 2-amino-1,3-propanediol (serinol) of formula (I):

(I)

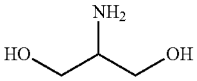

said process comprising the steps of:

i) reacting glycerol or glycerol 1,2-carbonate with urea at a temperature higher than or equal to 130° C. in the presence of a catalyst selected from Mg, MgO, $Mg(OMe)_2$, $Mg(OH)_2$ and $La_2O_3$ to provide 4-hydroxymethyl-2-oxazolidinone (serinol carbamate) of formula (II):

(II)

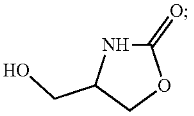

ii) hydrolyzing the serinol carbamate to obtain serinol; and iii) optionally converting the serinol into a salt thereof.

17. The process according to claim 16 wherein the molar ratio urea/glycerol or urea/glycerol 1,2-carbonate ranges from 1:1 to 4:1.

18. The process according to claim 16 wherein the ratio catalyst/glycerol or catalyst/glycerol 1,2-carbonate ranges from 0.1:1 to 1:1.

19. The process according to claim 16 wherein the reaction of step i) is carried out at a temperature ranging from 130° C. to 200° C.

20. A process for preparing Iopamidol of formula (III):

(III)

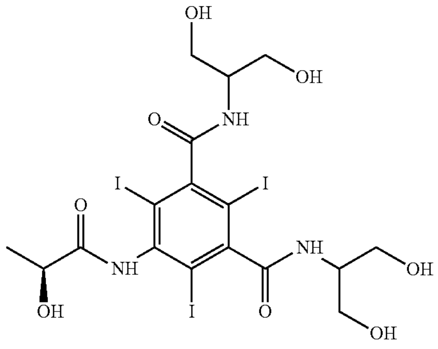

comprising the process according to claim 16 and further comprising the following steps:

iv) reacting the compound of formula (I) thus obtained with the compound of formula (V)

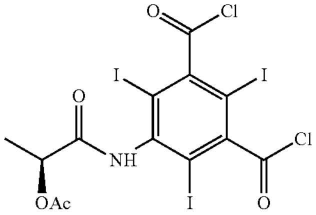 [SMILES: CC(=O)O[C@@H](C)C(=O)Nc1c(I)c(C(=O)Cl)c(I)c(C(=O)Cl)c1I]

and v) hydrolyzing the resultant compound of formula (IV)

(IV)

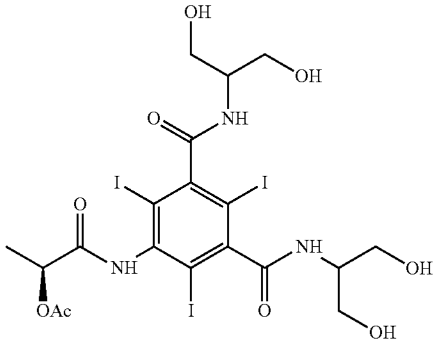

by removing the acetyl protecting group.

* * * * *